United States Patent [19]

Boos et al.

[11] Patent Number: 5,795,786
[45] Date of Patent: Aug. 18, 1998

[54] PROCESS AND REAGENT FOR THE SPECIFIC DETERMINATION OF LDL IN SERUM SAMPLES

[75] Inventors: Karl-Siegfried Boos, Gauting; Dietrich Seidel; Wolf-Dieter Engel, both of Feldafing; Angelika Kurrle-Weittenhiller, Tutzing, all of Germany

[73] Assignee: Boehringer Mannheim GmbH, Mannheim, Germany

[21] Appl. No.: 692,642

[22] Filed: Aug. 6, 1996

Related U.S. Application Data

[63] Continuation of Ser. No. 375,078, Jan. 17, 1995, abandoned, which is a continuation of Ser. No. 092,205, Jul. 15, 1993, abandoned.

[30] Foreign Application Priority Data

Jul. 16, 1992 [DE] Germany ............... 42 23 355.0

[51] Int. Cl.$^6$ .................................................. G01N 33/92
[52] U.S. Cl. .................. 436/71; 436/13; 436/17; 436/175
[58] Field of Search ................... 436/13, 71, 63, 436/825, 175, 17; 435/19

[56] References Cited

U.S. PATENT DOCUMENTS

| | | | |
|---|---|---|---|
| 4,486,531 | 12/1984 | Ziegenhorn et al. | 435/19 |
| 4,576,927 | 3/1986 | Kuroda et al. | 502/402 |
| 4,647,280 | 3/1987 | Maaskant et al. | 604/5 |
| 4,908,354 | 3/1990 | Seidel et al. | 514/21 |
| 5,242,833 | 9/1993 | Lawlor et al. | 436/71 |
| 5,286,626 | 2/1994 | Law et al. | 435/19 |

OTHER PUBLICATIONS

Harris *Quantitative Chemical Analysis*–2nd edition, 1987, p. 767.

Condensed Chemical Dictionary, 10th edition, 1981, pp. 24–25.

*Primary Examiner*—Maureen M. Wallenhorst
*Attorney, Agent, or Firm*—Felfe & Lynch

[57] ABSTRACT

A process and a reagent for the specific and direct determination of the LDL-fraction in the presence of other serum lipoproteins by adding a polymeric LDL-aggregating agent, followed by direct turbidimetric measurement of the LDL aggregate. Preferred are polymers which have a comb or brush type structure with the side groups having acid character, such as branched alkane sulfonic acids.

20 Claims, 7 Drawing Sheets

PROCESS AND REAGENT FOR THE SPECIFIC DETERMINATION OF LDL IN SERUM SAMPLES

This is a continuation application of application Ser. No. 08/375,078, filed Jan. 17, 1995, now abandoned, which was a continuation of application Ser. No. 08/092,205, filed Jul. 15, 1993, now abandoned.

FIELD OF THE INVENTION

The invention addresses a process for specific and direct determination of LDL in biological fluids. This is accomplished by adding an LDL-aggregating or agglutinating agent, which specifically aggregates LDL, even in the presence of other serum lipoproteins. Preferably, the LDL aggregating or agglutinating agent is a polymer has a comb or brush type structure.

BACKGROUND AND PRIOR ART

The determination of the LDL level in plasma and, especially, in serum is of great clinical importance: up to 80% of the total cholesterol contents is transported in the form of so-called low-density lipoproteins (LDLs of the β-fraction), and are, hence, part of those particles which today are considered to be paramount atherogenic component in lipid metabolism. Moreover, it is known that elevated plasma LDL concentrations have a direct endothelial damaging effect, which can be compared to a number of other problems caused by hypertension, hyperinsulinemia or endotoxins, and that cholesterol which was deposited in an astherosclerosis plaque was originally present in the form of LDL cholesterol in plasma.

Today, a number of processes exist for the quantitative determination of LDL and β-cholesterol in plasma and, especially, in serum (Mills, G. L., Lane , P. A., Weech, P. K., A Guidebook to Lipoprotein Technique, Elsevier, Amsterdam, 1984; Cremer, P., und Seidel, D., Deutsch. Gesell. Klin. Chem. Mitl. 21 (1990), 21–232).

A basic distinction is made between differentiating techniques such as ultracentrifugation and electrophoresis on the one hand, and precipitation techniques, on the other hand. The problem with the former is that they require expensive instrumentation and are also time-consuming. Today they are primarily used for reference and confirmation. Precipitation of LDL with high molecular substances containing mostly negative changes is, however, part of the routine work in laboratories. In clinical diagnostics, polyvinyl sulfate, polycyclical surface-active anions or heparin are frequently used as LDL precipitation reagents. They are, however, marked by several drawbacks. When heparin is precipitated in an acidic medium or with polycyclical anions in serum samples with a preceding or existing lipolytic activity, the LDL cholesterol measurements are falsely elevated. When dextran sulfate or polyvinyl sulfate, the agents of choice, are used, because they exhibit the highest possible precision in the LDL determination, serum samples with a preceding existing lipolytic activity show falsely depressed results. Moreover, measurements with dextran sulfate-containing precipitation reagents are also falsely depressed when high levels of free fatty acids or triglycerides are present in the sample to be analyzed. This problem occurs even more frequently with patients treated with heparin. Further, a disadvantages of all precipitation procedures is that in addition to LDL, the LDL-like lipoprotein Lp(a) is completely precipitated as well. The procedure is, hence, not entirely LDL-specific.

It is thus, an object of the invention to provide a simple and rapid process for the specific determination of LDL where there is no interference by other lipoprotein particles nor by elevated concentrations of triglycerides or free fatty acids or by heparinized samples.

SUMMARY OF THE INVENTION

The invention is a method for determining LDLs in a sample which contains other lipoproteins. This is accomplished by adding an LDL-specific aggregating agent to the sample and then determining the aggregation as a measurement of LDLs in the sample. In particularly preferred embodiments, the aggregating agent is a "comb" or "brush type" polymer, i.e., a poly(meth)acryl polymer having anionic side branches extending from the polymer backbone.

Figure 1:
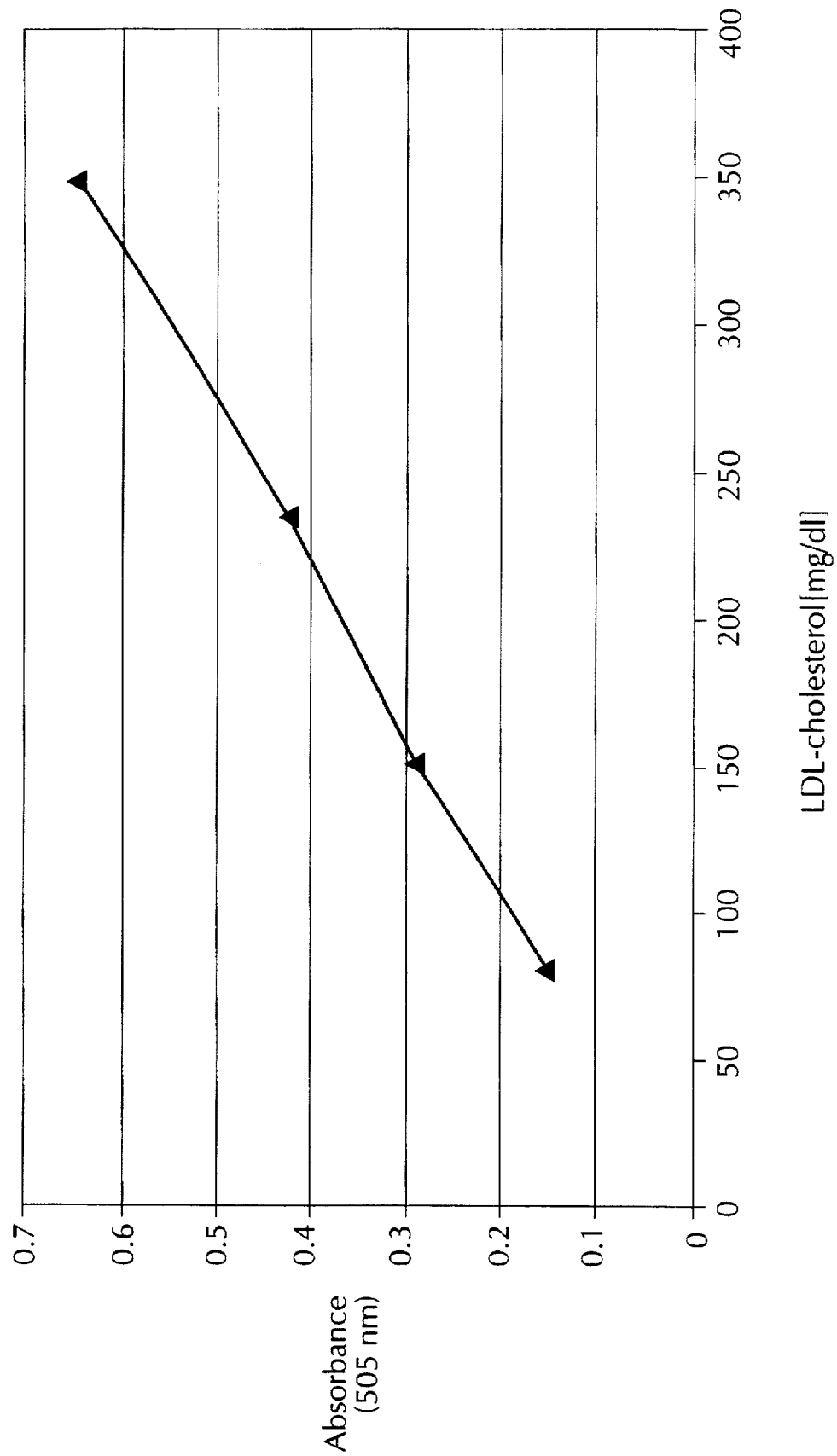
FIG. 1: Linearity of the measuring signal for the turbidimetric determination of LDL cholesterol.

(b) dextran sulfate precipitation reagent (Quantolip®).

DETAILED DESCRIPTION OF PREFERRED EMBODIMENTS

The comb or brush type polymers of the preferred embodiments of the invention are derived from acrylic acid ester monomers of formula:

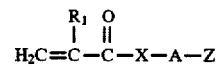

where $R_1$ is hydrogen or $C_1$–$C_6$ alkyl, preferably methyl; X is oxygen or —NH; A is a linear or branched alkyl chain of $C_1$–$C_{10}$, branched chains being preferred, and Z is selected from the group consisting of $COO^-$, $SO_3^-$, and $HPO_3^-$.

The individual units of the resulting polymer will lack the double bond of the monomer depicted supra. Thus, the polymers as described herein are represented by the formula:

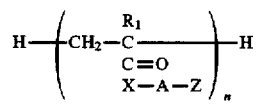

where each of $R_1$ X, A and Z are as above, and "n" is any number as long as it is 2 or more.

Particularly suitable are homopolymers of 2-acrylamido-2-methyl-1-propane sulfonic acid, 2-acrylamido glycolic acid and/or acrylic acid (2-phospho-1, 1-dimethylethylamide and/or copolymers of the said monomers.

The brush anionic comb polymers of the invention have a preferred molecular weight of $2 \times 10^4$ to $5 \times 10^6$ dalton, the particularly preferred weight being approximately $5 \times 10^5$ daltons as determined by gel permeation chromatography.

The anionic comb polymers of the invention can be produced by employing procedures known to the expert such as solution, suspension or emulsion polymerization (Meth. d. Organ. Chemie (Houben-Weyl), Bd. E 20, Makrom. Stoffe, Thieme Verlag, Stuttgart, 1987). The preferred procedure is solvent polymerization as described, for example, in Polymer 31 (1990), 1269–1276 (Huglin and Rego). The polymerization procedure can be accelerated by conventional initiators which are included in aqueous systems and form free radicals, especially peroxides, persulfates or persulfate/bisulfite or corresponding azo combinations. These procedures are also known to the expert. The preferred initiator for the preparation of the anionic comb polymer of the invention is ammonium peroxodisulfate.

The concentration of polyanions used in accordance with the invention is between 0.01 to 0.50 mg/ml, preferably between about 0.05 and about 0.30 mg/ml. Particularly suitable is a range between 0.07 to 0.20 mg/ml.

A buffering substance can also be used in the invention. Generally, those buffering substances can be used for the determination of the invention whose buffering capacity is in the weakly acid, neutral or weakly alkaline pH range. Particularly suitable substances are sodium acetate and/or citric acid. The pH value for the determination when one of these buffer substance is used preferably ranges between pH 5 and 6, a range between 5.10–5.50 being particularly preferred, and a range between 5.20–5.30 being especially preferred. The concentration of the buffer should range between 0.03–0.15 mol/l. A particularly preferred concentration range is between 0.05 to 0.07 mol/l.

Another preferred embodiment includes the use of a Tris-HCl buffer, a bis[2-hydroxyethyl]imino-tris |hydroxymethyl|methane (bis-tris) or a 1-[N,N-bis(2-hydroxyethyl)-amino|-2-propanol (BAP) buffer in the presence of bivalent metal ions, the concentration of the buffer ranging between 0.01 to 0.15 mol/l, the concentration of the metal salt generating the bivalent ion between 0.01–0.20 mol/l and a pH range between 5.5 to 9.0. In a particularly preferred embodiment, the concentration of the buffer ranges from about 0.02 to about 0.1 mol/l, the concentration of the metal salts from about 0.02 to about 0.15 mol/l and the pH range between 7.0–8.5. Generally, it is possible to use the salts of all known bivalent metal ions, particularly preferred ions being $Mg^{2+}$, $Ca^{2+}$, $Mn^{2+}$ and $Cu^{2+}$. More particularly preferred ions are $Mg^{2+}$ and $Ca^{2+}$. The concentration of the polyanions must be selected as indicated above.

Another subject matter of the invention is a reagent which contains the polymers of the invention and a buffer substance in a pH range between 5 and 9. The amount of polymer ranges between 0.01 to 0.50 mg/ml reagent solution; preferably there is added poly-(2-acrylamido-2-methyl-1-propane sulfonic acid) (PAMPS), poly-acrylic acid- (2-phospho-1, 1-dimethyl ethylamide) (PAP), poly-2-acrylamido glycollic acid (PAAG), poly-(2-acrylamido-2-methyl-1-propane sulfonic acid-CO-2-acrylamido glycollic acid) |P(AMPS-AAG)| and/or corresponding copolymers and/or corresponding poly(meth) acrylic acid ester in a concentration range of 0.05–0.30 mg/ml, particularly preferred in a concentration range between 0.07–0.20 mg/ml. Sodium acetate, TRIS-HCl, bis-TRIS, BAP and/or citric acid have proven to be particularly suitable buffer substances. The preferred concentration of the buffer ranges between 0.01–0.15 mol/l.

For the determination of LDL, the pH range of the reagent is between 5.1 and 9.0, preferably between pH 5.1 and 5.5 or between pH 7.0 and 8.5. The assay temperature can vary between 10° and 40° C.; a preferred temperature is approximately 37° C.

The volume ratio between sample to be analyzed and reagent solution is variable. Ratios of 1:1 to 1:100 have proven to be suitable. In a preferred manner, approximately 10 volume parts of serum sample (e.g. 10 µl) are mixed with 350 volume parts reagent solution (e.g. 350 µl).

As compared to known precipitation reagents, the LDL-specific aggregation or agglutionation that was realized via the anionic comb polymers of the invention has the following advantages:

1. Rapid determination without requiring sample pretreatment (approximately 1–10 min).
2. Formed aggregate is present in a stable condition and can, hence, be directly and reproducibly measured.
3. The determination of LDL cholesterol is linear in a very broad range (50–350 mg/dl LDL cholesterol).
4. Except for LDL, other apoprotein B-containing lipoproteins (very low density lipoproteins (VLDL), Lp(a)) and/or chylomicrons) do not interact with the polyanions of the invention and are, hence, not detected.

In a manner which has so far been unknown, the process and the reagent of the invention, lead to a complete agglutination of the LDL particles within 1 to 5 minutes without separation of the other lipoprotein fractions. It is, therefore, also possible to employ an analyzer or a simple photometer (turbidimetric) for the determination of the LDL concentration or the LDL cholesterol, which is desirable in routine analysis work. Moreover, it is also possible to determine the apoprotein B-100 and/or other molecular components of the LDL particles that are present in the LDL agglutinate.

The broad measuring range in which the method of the invention generates a linear measuring signal includes the diagnostically relevant range, in particular the one for elevated LDL values (>190 mg/dl), which includes the advantage of requiring only a one-point calibration procedure. As another consequence of the extended linear range, elevated LDL levels can also be quantitatively monitored in a more precise way without requiring corresponding complicated reference procedures such as lipoprotein electrophoresis or ultracentrifugation.

The process and the reagent of the invention agglutinates LDL, but not LDL-like Lp(a). This is surprising as all known LDL precipitation reagents also precipitate the Lp(a) fraction almost quantitatively. With the present invention it is, hence, also possible to determine the Lp(a) fraction in a simple manner by reductively cleaving the Lp(a) portion of the Lp(a) particle which is connected via a disulfide bridge after LDL agglutination and determination in accordance with the invention in a manner which is known to the expert. By forming the difference, it is then possible to determine the contents of lipoprotein(a).

Moreover, in order to implement the process of the invention on an analyzer, the individual reaction components can also be impregnated on or in a carrier material or be covalently bound. The carrier material can be material which is absorbent, capable of swelling or forming a film, e.g. carrier materials that are known to be used with test strips such as paper or similar fleece materials such as tea bag paper. The reaction components can be distributed on several carriers that are interconnected or may themselves serve as carrier material.

The following examples illustrate the invention in greater detail:

EXAMPLE 1

(a) Preparing poly-(2-acrylamido-2-methyl-l-propane sulfonic acid) (PAMPS) by radical polymerization 8.412 g of 2-acrylamido-2-methyl-l-propane sulfonic acid (AMPS) are dissolved in 100 ml redistilled water, and the solution is exposed to nitrogen for a period of 30 min or treated in an ultrasonic bath. A solution of 22.8 mg ammonium peroxodisulfate in 100 ml redistilled water which had previously been exposed to nitrogen for a period of 30 min or was treated in an ultrasonic bath is added to this batch, while being heavily stirred, and heated up to 50° C. After 30 min, the temperature is raised to 70° C. and the reaction mixture is reduced to a volume of 20 ml. Using a dialysis tube with an exclusion limit of 12 to 14,000 dalton, this reaction mixture is dialyzed against redistilled water for a period of 4 days. The dialysate is evaporated until dry and produces crystalline PAMPS with an average molecular weight of $5 \times 10^5$ dalton (gel permeation chromatography).

Analogously, the following anionic comb polymers were produced:
(b): Poly-methacrylic acid-(2-sulfopropyl ester) (PMAS),
(c): Poly-2-acrylamido glycollic acid (PAAG),
(d): Poly-acrylic acid as determined by 2-phospho-1,1-dimethyl-ethylamide (PAP) and
(e): Poly-(2-acryamido-2-methyl-1-propane sulfonic acid-CO-2-acrylamido glycollic acid) [P(AMPS-AAG)], from AMPS and AAG in a ratio of 1:1.

EXAMPLE 2

Determination of LDL cholesterol

Reagent solution:

0.15 mg/ml PAMPS (free acid)

0.05 mol/l sodium acetate/citric acid, pH 5.20 (acetic acid or citric acid (0.05 mol/l) were used to adjust the pH).

Sample: serum

10 µl serum sample were mixed with 350 µl reagent solution at 37° C. After 1–2 minutes, the absorbance increase which is a consequence of the turbidity is determined at 505 nm. Calibration for LDL cholesterol is carried out with a serum sample of a known LDL cholesterol contents (standard). Sample blank correction should be carried out particularly when lipemic serum samples are analyzed.

TABLE 1

| Absorbance | LDL cholesterol [mg/dl] |
|---|---|
| 0.145 | 81 |
| 0.2864 | 150 |
| 0.4217 | 234 |
| 0.6433 | 348 |

| Regression analysis: | |
|---|---|
| Constant | 0.528 |
| Standard deviation Y | 5.577 |
| R squared | 0.998 |
| Number of measurements | 4 |
| Degrees of freedom | 2 |
| X-coefficient | 541.891 |
| Standard deviation d. | 15.185 |
| R = 0.999 | |

2.1 LDL cholesterol determination (PAMPS) depends upon the pH value

The processes were carried out as described in example 2. However, three additional reagent mixtures, the pH values being 5.30, 5.40 and 5.50, respectively, were prepared.

Figure 2:
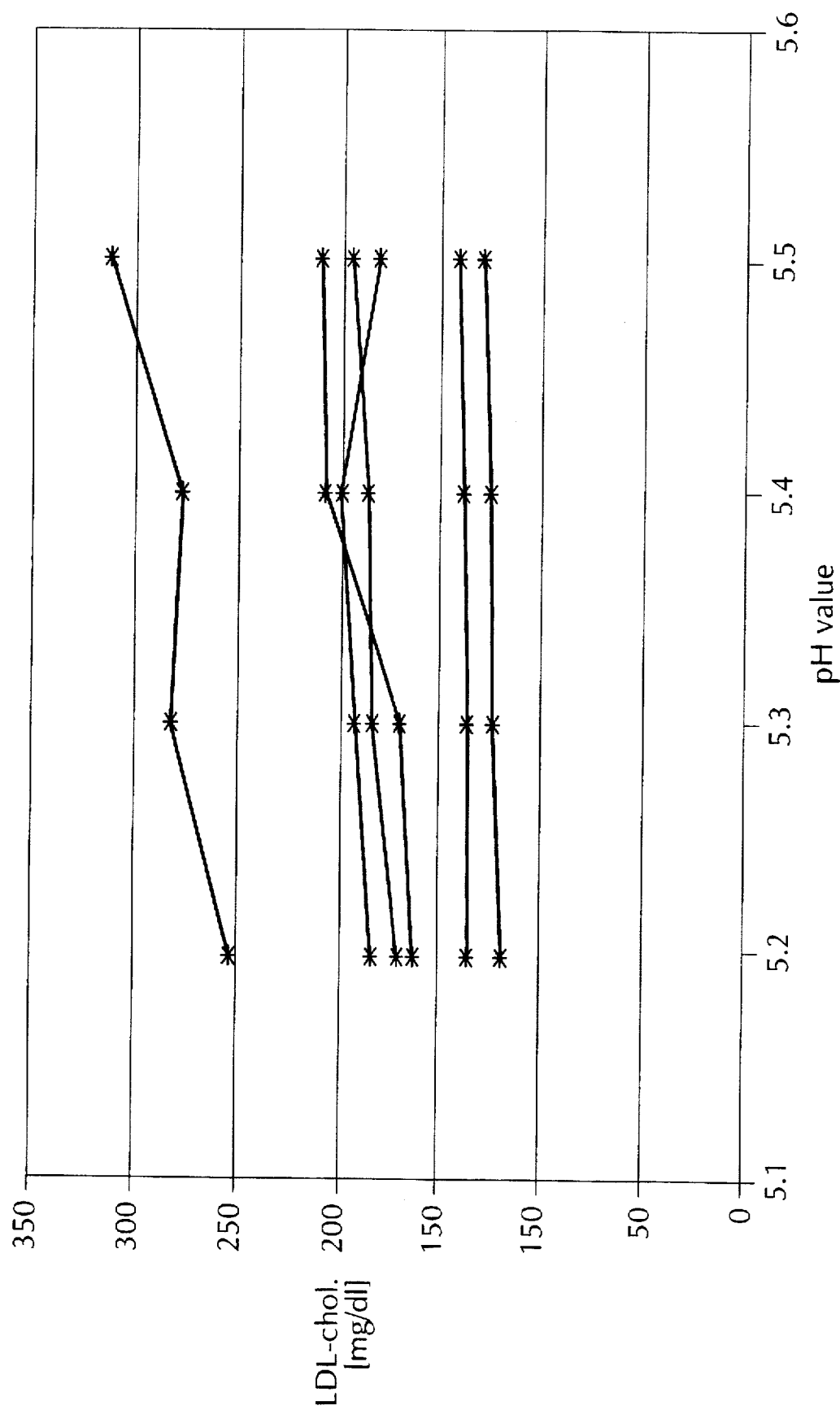
FIG. 2: pH dependency of the process of the invention, buffer concentration: 0.15 mg/ml sodium acetate/0.07 mol/l citric acid.
Figure 3:
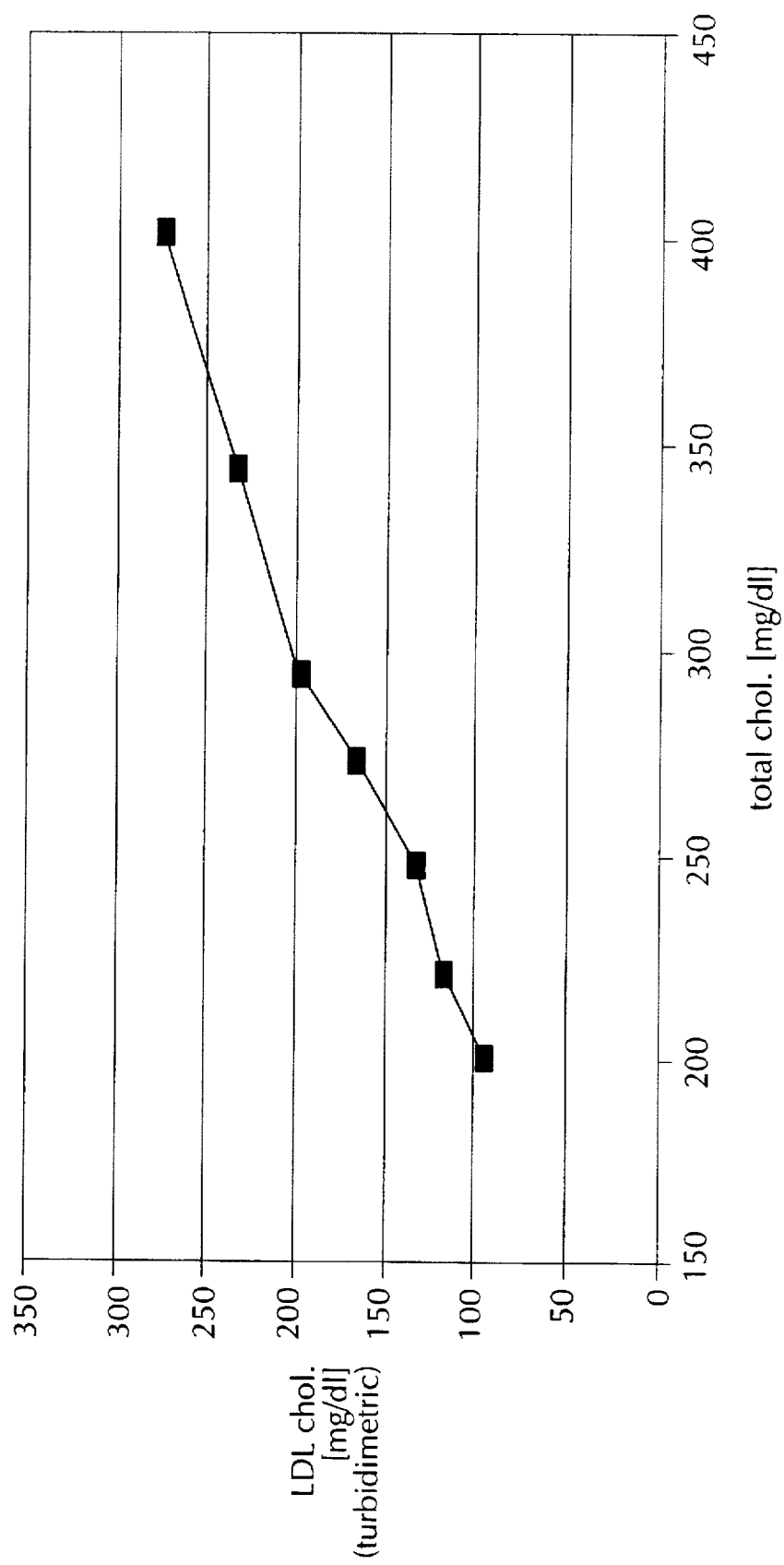
FIG. 3: Normal serum samples spiked up with LDL (ultra centrifugation (UC).
Figure 4:
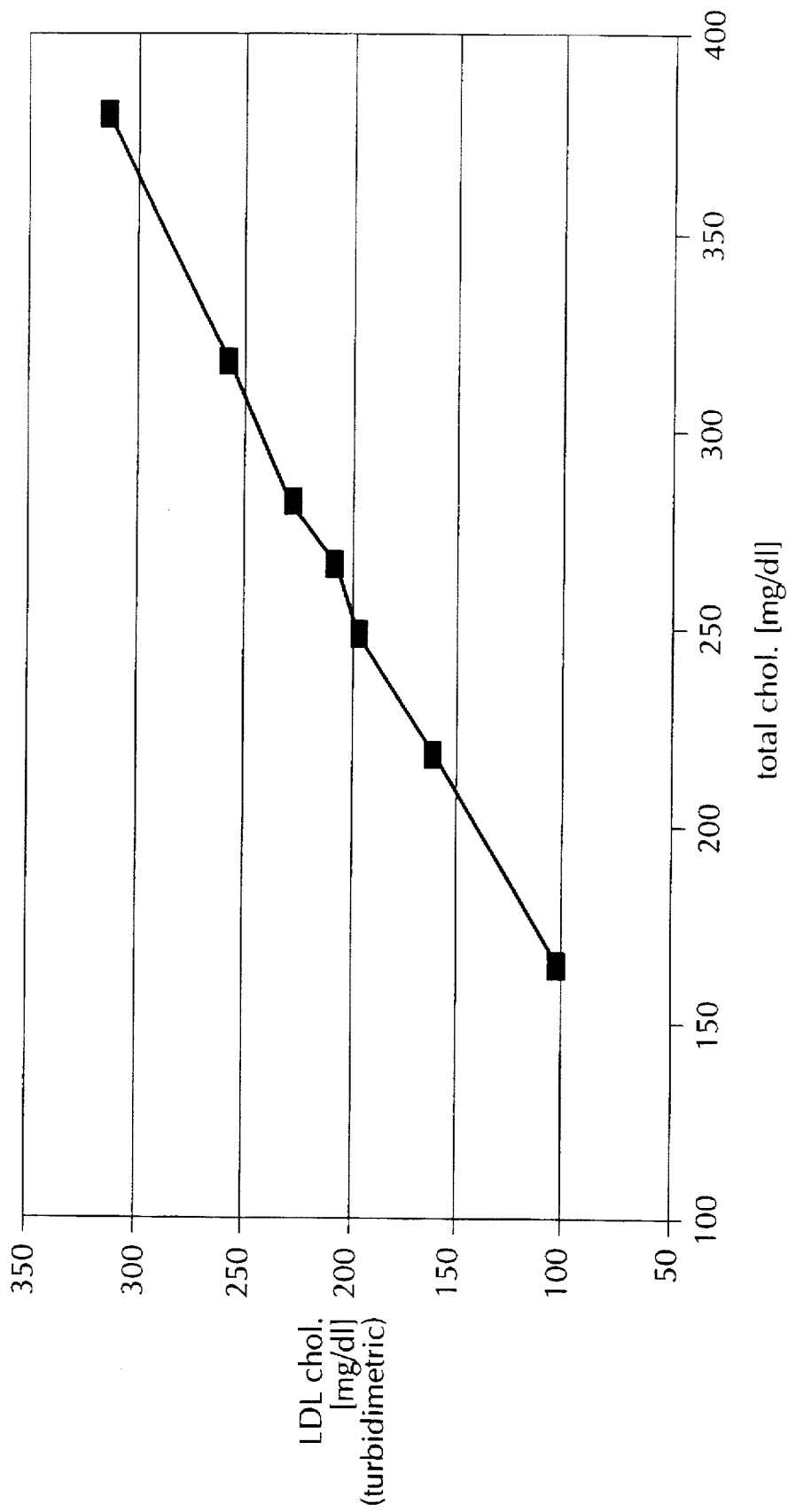
FIG. 4: Triglyceride-rich serum samples spiked up with LDL (UC).

The corresponding results are given in Table 2 and FIG. 2. In addition, Table 2 also contains the measurement results that were obtained with the prior art process (Quantolip®, manufactured by Immuno GmbH, Heidelberg, FRG) and the respective triglyceride (TG) contents.

TABLE 2

| Total cholesterol [mg/dl] | TG [mg/dl] | LDL cholesterol Quantolip® [mg/dl] | Turbidimetric LDL cholesterol determination (0.15 mg/ml 0.07 M sodium acetate) | | | |
|---|---|---|---|---|---|---|
| | | | pH 5.2 [mg/dl] | pH 5.3 [mg/dl] | pH 5.4 [mg/dl] | pH 5.5 [mg/dl] |
| 236 | 142 | 153 | 134 | 134 | 135 | 138 |
| 204 | 235 | 124 | 118 | 121 | 122 | 125 |
| 280 | 126 | 177 | 183 | 190 | 200 | 180 |
| 299 | 161 | 200 | 169 | 182 | 186 | 194 |
| 269 | 131 | 208 | 162 | 168 | 206 | 207 |
| 372 | 241 | 261 | 253 | 280 | 275 | 309 |
| 215 | 141 | 146 | 151 | 162 | 179 | 185 |

LDL cholesterol determination: dependency upon the LDL contents (spiked up with LDL The samples with human serum were spiked up with LDL (density fraction between 1.006 and 1.063 g/ml), which was isolated with the aid of an ultracentrifuge according to Wieland, H. and Seidel, D. (Clin. Chem., 28 (1982), 1335–1337). The determination was performed as described in example 2.

TABLE 3

| Normal serum sample spiked up with LDL (UC) | | | | |
|---|---|---|---|---|
| Sample | Total cholesterol [mg/dl] | Diff. to IV | TG [mg/dl] | PAMPS (P1) turbidim. LDL chol. [mg/dl] | Diff. to IV |
| IV | 201 | | 92 | 92 | |
| + LDL | 221 | 20 | 96 | 114 | 22 |
| + LDL | 248 | 47 | 94 | 131 | 39 |
| + LDL | 273 | 72 | 98 | 164 | 72 |
| + LDL | 295 | 96 | 101 | 195 | 103 |
| + LDL | 345 | 144 | 106 | 2332 | 140 |
| + LDL | 401 | 200 | 113 | 274 | 182 |
| | Expected value | | | | Actual value |

Recovery (LDL cholesterol)

Mean value: 98%

Pl: 0.05 mol/l sodium acetate/citric acid buffer, pH 5.20

IV=initial value 2.3 LDL cholesterol determination: dependency upon the LDL contents (spiked up with LDL) with a triglyceride (TG)-rich serum sample The serum samples were spiked up with LDL as indicated under 2.1.

TABLE 4

| TG-rich serum samples spiked up with LDL (UC) | | | | |
|---|---|---|---|---|
| Sample | Total cholesterol [mg/dl] | Diff. to IV | TG [mg/dl] | PAMPS Turbidim. LDL chol. determin. [mg/dl] | |
| | | | | Buffer P1 | Diff/IV |
| IV | 166 | | 859 | 102 | |
| + LDL | 219 | 47 | 836 | 160 | 58 |
| + LDL | 249 | 83 | 828 | 198 | 96 |

TABLE 4-continued

TG-rich serum samples spiked up with LDL (UC)

| Sample | Total cholesterol [mg/dl] | Diff. to IV | TG [mg/dl] | PAMPS Turbidim. LDL chol. determin. [mg/dl] Buffer P1 | Diff./IV |
|---|---|---|---|---|---|
| +LDL | 266 | 100 | 773 | 208 | 106 |
| +LDL | 282 | 116 | 787 | 227 | 125 |
| +LDL | 317 | 151 | 736 | 257 | 155 |
| +LDL | 379 | 213 | 682 | 315 | 213 |
|  | Expected value |  |  |  | Actual value |

Recovery (LDL cholesterol)
Mean value: 108%

EXAMPLE 3

Method comparison 3.1 The method of the invention (PAMPS) was compared to an ultracentrifugation method (UC. reference method)

The procedure was carried out according to Armstrong, V. W. and Seidel, D. (Ärztl. Lab. 31 (1985), p. 325–330).

Figure 5:
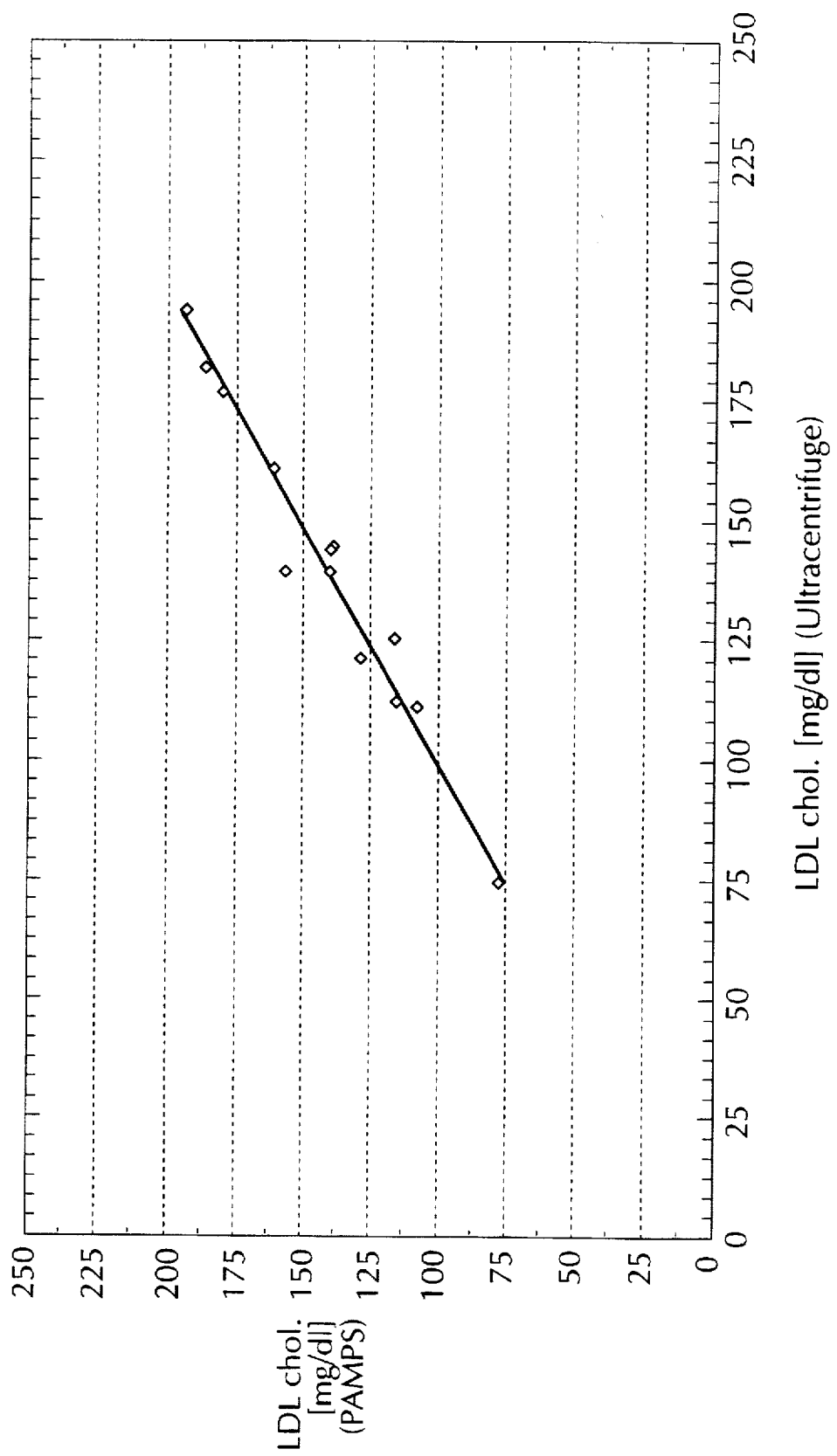
FIG. 5: Method comparison: one embodiment of the invention (PAMPS) and prior art ultracentrifuge (Uc).

Results for LDL cholesterol are given in Table 5 and FIG. 5.

TABLE 5

Method comparison: the method of the invention (PAMPS)/ ultracentrifugation (UC)

| UC LDL cholesterol [mg/dl] | PAMPS (buffer as in example 2.2) LDL cholesterol [mg/dl] |
|---|---|
| 74 | 78 |
| 111 | 108 |
| 112 | 115 |
| 125 | 116 |
| 121 | 128 |
| 144 | 139 |
| 143 | 140 |
| 139 | 140 |
| 139 | 157 |
| 160 | 162 |
| 176 | 181 |
| 181 | 188 |
| 193 | 195 |

Regression analysis:

| Constant | −1.166 |
|---|---|
| Standard deviation Y | 6.959 |
| R squared | 0.961 |
| Number of measurements | 13 |
| Degrees of freedom | 11 |
| X-coefficient | 1.024 |
| Standard deviation d. | 0.061 |
| R = 0.980 | |

3.2 The method of the invention (RAMPS) was compared to the dextrane sulfate method The determination of LDL cholesterol with PAMPS was carried out as described under example 2. For the determination of LDL cholesterol with dextrane sulfate, Quantolip® manufactured by Immuno GmbH, Heidelberg, was used as specified by the manufacturer.

Figure 6:
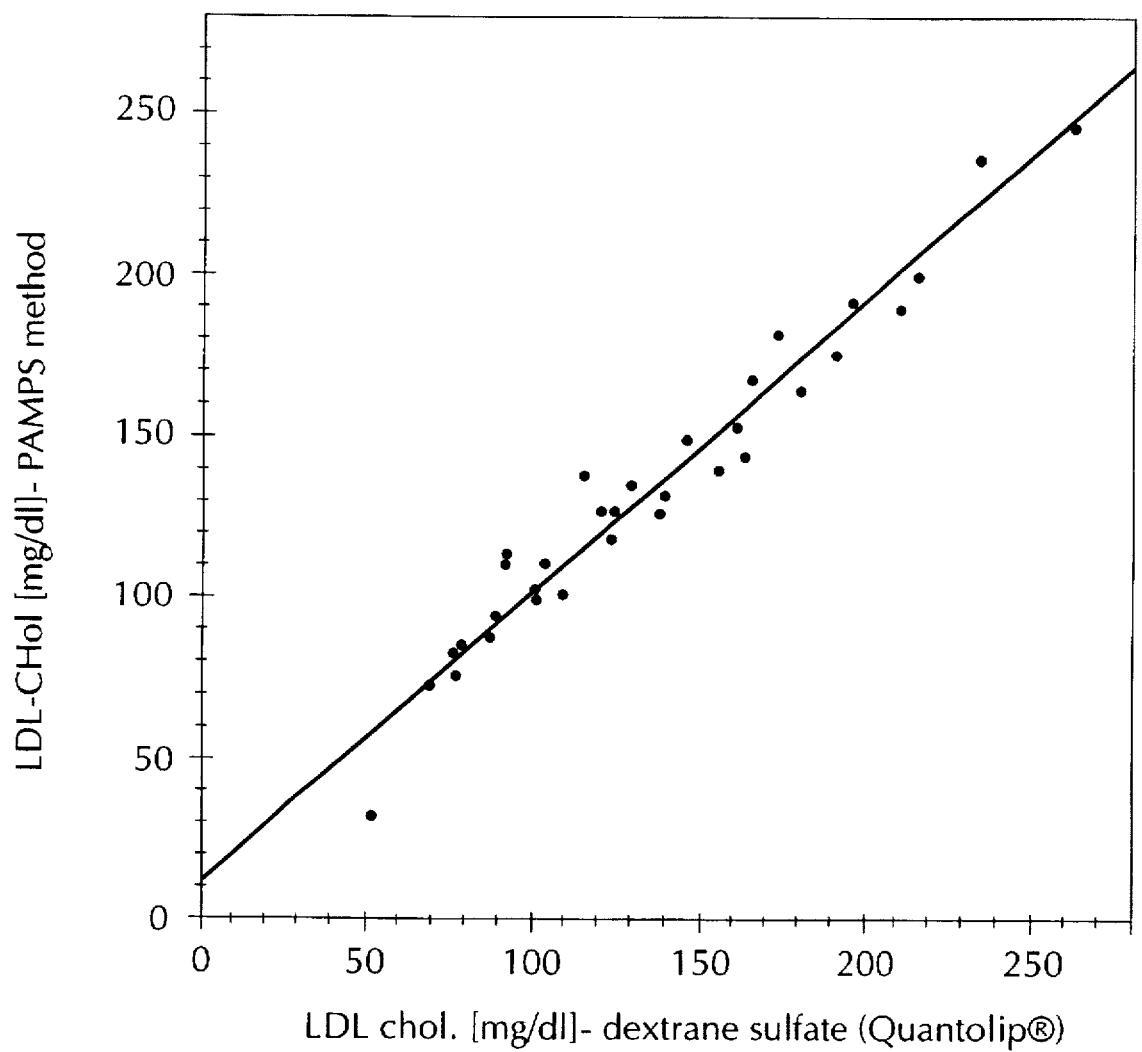
FIG. 6: LDL cholesterol determination in accordance with one embodiment of the invention (PAMPS) and with prior art dextran sulfate.
Figure 7:
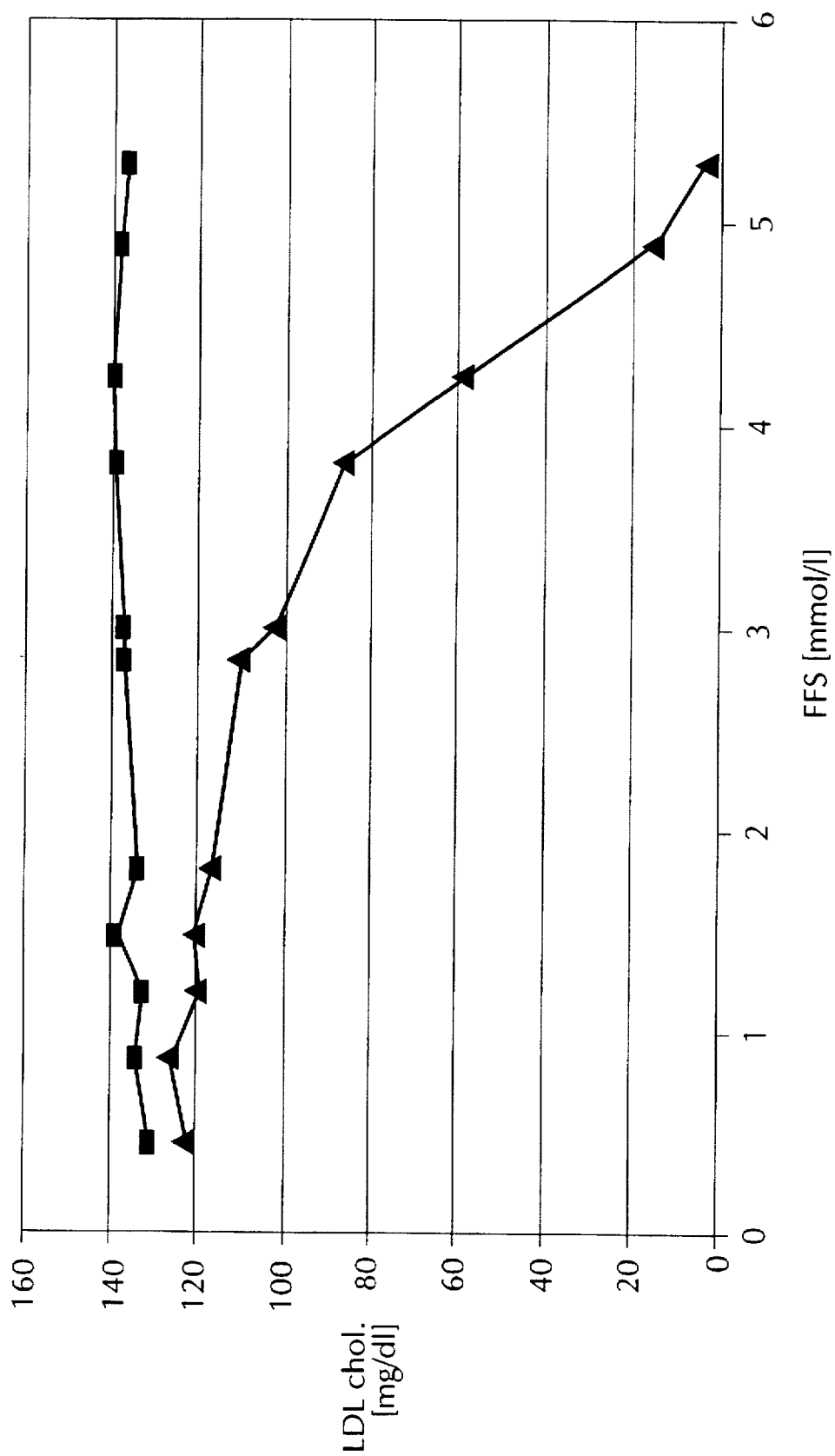
FIG. 7: LDL cholesterol levels determined with (a) the PAMPS embodiment of the invention (0.05 mol/l sodium acetate/citric acid, pH 5.20)

The results of the comparative determination of LDL cholesterol are given in Table 6 and FIG. 6.

TABLE 6

| Total cholesterol [mg/dl] | TG [mg/dl] | LDL cholesterol after dextrane sulfate precipitation [mg/dl] | Turbidimetric LDL cholesterol determ. buffer PAMPS (P1) [mg/dl] |
|---|---|---|---|
| 88 | 115 | 52 | 32 |
| 175 | 449 | 69 | 74 |
| 126 | 184 | 77 | 85 |
| 136 | 177 | 78 | 76 |
| 147 | 159 | 80 | 87 |
| 195 | 137 | 88 | 90 |
| 154 | 128 | 89 | 94 |
| 200 | 177 | 93 | 111 |
| 181 | 79 | 101 | 104 |
| 190 | 58 | 105 | 111 |
| 185 | 150 | 124 | 119 |
| 206 | 77 | 146 | 150 |
| 242 | 98 | 155 | 141 |
| 266 | 148 | 173 | 182 |
| 280 | 134 | 209 | 190 |
| 327 | 112 | 214 | 200 |

Regression analysis:

| Constant | 9.758 |
|---|---|
| Standard deviation Y | 10.438 |
| R squared | 0.952 |
| Number of measurements | 16 |
| Degrees of freedom | 14 |
| X-coefficient | 0.911 |
| Standard deviation d. | 0.054 |
| R = 0.976 | |

3.3 Influence of free fatty acids (FFA) on the determination of LDL cholesterol

When dextran sulfate (DS, Quantolip®, manufactured by Immuno GmbH, Heidelberg) or the polyvinyl sulfate precipitation reagent (Boehringer Mannheim) were used undesired interference occurs in the LDL cholesterol determination when increased concentrations of free fatty acids (FFA) are present in the material to be analyzed. Serum levels of free fatty acids greater than 2 mmol/l (normal range: 0.3 to 1.0 mmol/l) interfere with the interaction between the LDL particles and these precipitation reagents thus leading to an incomplete LDL precipitation and, hence, to falsely depressed measurements. This disadvantageous property also occurs when the material to be analyzed had been stored too long or in too warm an environment due to an increased in vitro lipolysis (Seidel, D., Armstrong, V. W., Cremer, P., Internist 28 (1987), 606–614).

The samples with human serum were enriched with free fatty acids (FFA: stearic acid, palmitic acid) according to Spector and Hoak, Anal. Biochem. 32 (1969), 297–302.

TABLE 7

| FFA [mmol/l] | LDL cholesterol DS precipitation [mg/dl] | LDL cholesterol PAMPS [mg/dl] |
|---|---|---|
| 0.45 | 123 | 131 |
| 0.87 | 126 | 134 |
| 1.2 | 119 | 132 |
| 1.48 | 120 | 139 |
| 1.81 | 116 | 133 |
| 2.84 | 111 | 136 |
| 3 | 103 | 136 |
| 3.8 | 88 | 139 |
| 4.24 | 59 | 140 |
| 4.88 | 14 | 138 |
| 5.28 | 3 | 137 |

3.4 Coagglutination of Very Low Density Lipoproteins (VLDL)

In order to investigate the selective agglutination properties of the reagent of the invention with respect to LDL particles in the presence of apoprotein B-containing VLDL particles, one volume part of VLDL (cholesterol: 153 mg/dl; triglycerides: 488 mg/dl), which has been isolated in an ultracentrifuge in a known manner, was added to 1 volume part of a serum sample (total cholesterol: 334 mg/dl; triglycerides: 107 mg/dl; LDL cholesterol 241 mg/dl).

A subsequent turbidimetric determination of the LDL cholesterol concentration with the reagent of the invention (PAMPS) yielded a value of 125 mg/dl. The method of the invention is, consequently, very selective with respect to the agglutination of apoprotein B-containing LDL particles.

When using the dextran sulfate precipitation method (Quantolip®), the initial value for the LDL cholesterol concentration was determined as 240 mg/dl. The serum to which VLDL was added in a ratio of 1:1 (v/v) yielded a value of 49 mg/dl. This falsely low LDL cholesterol value is a result of the incomplete LDL precipitation in triglyceride and VLDL-rich serum when using a dextrane sulfate precipitation reagent, which is known to the expert.

3.5 Coagglutination of Lp(a)

1 volume part of a Lp(a)-free normaglyceridemic serum (triglycerides: 120 mg/dl with a total cholesterol concentration of 104 mg/dl and a LDL cholesterol concentration of 104 mg/dl and a LDL cholesterol concentration of 71 mg/dl determined with the method of the invention was added to 1 volume part of isolated Lp(a) [cholesterol concentration: 120 mg/dl; Armstrong, V. W., Walli, A. K., Seidel, D. J. Lipid Research, 1985, 26, 1314–1323]. The subsequent turbidimetric determination of the LDL cholesterol concentration with the reagent of the invention (PAMPS) yielded a value of 34 mg/dl.

When using the dextran sulfate precipitation method (Quantolip®), the initial value for the LDL cholesterol concentration was determined as 72 mg/dl. The serum to which Lp(a) was added in a ratio of 1:1 (v/v) yielded a value of 96 mg/dl, demonstrating that the dextrane sulfate reagent also quantitatively precipitates the Lp(a) fraction in an undesired manner. The method of the invention, hence, agglutinates advantageously no Lp(a) particles and does not erroneously detect these as LDL particles.

We claim:

1. Method for directly determining an LDL fraction in the presence of other serum lipoproteins, comprising adding to an LDL containing sample to be analyzed, and LDL-specific aggregating agent which is a poly(meth)acryl polymer having anionic side branches extending from the polymer backbone, and a buffering agent, whereby said LDL fraction and said poly(meth)acryl polymer form an LDL-aggregate complex which precipitates or separates from a dissolved state, and thereby determining said formed LDL-aggregate complex.

2. The method of claim 1, wherein said poly(meth)acryl polymer consists of monomers of formula

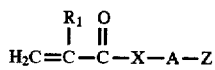

wherein $R^1$ is hydrogen or C1–C6 alkyl, X is oxygen or —NH, A is linear or branched C1–C10 alkyl, and Z is $COO^-$, $SO_3^-$, or $HPO_3^-$.

3. The method of claim 2, wherein $R^1$ is methyl.

4. The method of claim 2, wherein A is a branched chain.

5. The method of claim 1, wherein said LDL-specific aggregating agent has a molecular weight of from about 20,000 to about 5,000,000 daltons as determined by gel permeation chromatography.

6. The method of claim 1, comprising determining said LDL fraction at a pH of from 5 to 9.

7. The method of claim 1, comprising adding said LDL-specific aggregating agent at a concentration of from about 0.05 to about 0.30 mg/ml.

8. The method of claim 1, wherein said poly(meth)acryl polymer is poly-(2-acrylamido-2-methyl-1-propane sulfonic acid), poly-2-acrylamido-glycolic acid, poly-acrylic acid-(2-phospho-1,1-dimethyl-ethyl amide), poly-(2-acrylamido-2-methyl-1-propane sulfonic acid-CO-2-acrylamido glycolic acid), a copolymerisate of said poly(meth)acryl polymer containing a plurality of different monomers, a poly(meth)acryl acid ester of said poly(meth)acryl polymer, or a copolymerisate of said poly(meth)acrylic acid ester.

9. The method of claim 1, wherein said buffering agent is sodium acetate, TRIS-HCl bis[hydroxyethyl]imino-tris [hydroxyethyl]methane, 1-[N,N-bis(2-hydroxyethyl)-amino]-2-propanol, or citric acid.

10. The method of claim 1, comprising adding said buffering agent in an amount ranging from about 0.01 to about 0.15 mol/l.

11. The method of claim 1, further comprising adding a salt containing a divalent metal ion.

12. The method of claim 1, wherein said divalent metal ion is added at a concentration of from about 0.01 to about 0.20 mol/l.

13. The method of claim 1, comprising determining said formed LDL-aggregate complex at a temperature of from about 10° C. to about 40° C.

14. The method of claim 1, comprising determining said formed LDL-aggregate complex at a time from about 1 minute to about 10 minutes after adding said LDL specific aggregating agent to said sample.

15. The method of claim 1, wherein said poly(meth)acrylic polymer comprises a monomer of 2-acrylamido-2-methyl-1-propane sulfonic acid, acrylic acid-2-phospho-1,1-dimethyl ethylamide, 2-acrylamidoglycolic acid, or a (meth)acrylic acid ester of said monomer.

16. The method of claim 1, further comprising determining a specific component of said formed LDL-aggregate complex.

17. The method of claim 16, wherein said specific component is a low density lipoprotein, LDL-cholesterol, or LDL-apoliprotein B.

18. The method according to claim 1 wherein said sample is at a working temperature which ranges between 10° C. and 40° C., and said method comprises determining the LDL-aggregate complex turbidometrically.

19. The method according to claim 18, wherein said working temperature is about 37° C.

20. Method for determining lipoprotein (a) in a sample containing an LDL fraction, comprising:

(i) adding to a sample to be analyzed containing LDL and lipoprotein (a) an LDL-specific aggregating agent and a buffering agent, to form a LDL-aggregate complex containing LDL and lipoprotein (a);

(ii) measuring said LDL -aggregate complex to obtain a first value;

(iii) treating said LDL -aggregate complex to cleave lipoprotein (a) therefrom, (iv) measuring resulting aggregates following said treating to obtain a second value, and;

(v) subtracting said second value from said first value to determine lipoprotein (a) in said sample.

* * * * *

UNITED STATES PATENT AND TRADEMARK OFFICE
CERTIFICATE OF CORRECTION

PATENT NO. : 5,795,786
DATED : Aug. 18, 1998
INVENTOR(S) : Boos, et al

It is certified that error appears in the above-identified patent and that said Letters Patent is hereby corrected as shown below:

In column 6, line 40, change "2332" to --232--

Signed and Sealed this

Twenty-seventh Day of June, 2000

Attest:

Q. TODD DICKINSON

Attesting Officer          Director of Patents and Trademarks